United States Patent [19]

Failla et al.

[11] Patent Number: 4,476,865

[45] Date of Patent: Oct. 16, 1984

[54] NON-METALLIC, BIO-COMPATIBLE HEMOSTATIC CLIPS

[75] Inventors: Stephen J. Failla, Chester; Stephen J. Jewusiak, Denville; William J. Zwaskis, Carteret, all of N.J.

[73] Assignee: Ethicon, Inc., Somerville, N.J.

[21] Appl. No.: 348,399

[22] Filed: Feb. 12, 1982

[51] Int. Cl.³ .......................................... A61M 17/12
[52] U.S. Cl. .................................. 128/326; 128/346; 251/10
[58] Field of Search ...................... 128/325, 326, 346; 251/9, 10

[56] References Cited

U.S. PATENT DOCUMENTS

| 2,013,269 | 9/1935 | Ginsburg | 128/346 |
| 2,626,608 | 1/1953 | Garland | 128/346 |
| 3,040,749 | 6/1962 | Payton | 128/346 |
| 3,713,622 | 1/1973 | Dinger | 251/10 |
| 3,926,195 | 12/1975 | Bleier | 128/346 |

FOREIGN PATENT DOCUMENTS

| 1957855 | 5/1971 | Fed. Rep. of Germany | 128/325 |
| 2054027 | 2/1981 | United Kingdom | 128/326 |

Primary Examiner—Dalton L. Truluck
Attorney, Agent, or Firm—Robert L. Minier

[57] ABSTRACT

A hemostatic clip fabricated from absorbable or non-absorbable bio-compatible polymeric materials.

The clips have a pair of leg members joined by a hinge at their proximal ends and terminating at their distal ends in latch means. The leg members have complementary configurations which urge the hook member towards the hinge means when the clip is in the closed position.

4 Claims, 11 Drawing Figures

NON-METALLIC, BIO-COMPATIBLE HEMOSTATIC CLIPS

The present invention relates to hemostatic clips and more particularly to hemostatic clips fabricated from bio-compatible polymeric materials which may be absorbable or non-absorbable in body tissue.

BACKGROUND OF THE INVENTION

In many surgical procedures, it is often necessary to ligate a plurality of vessels within the surgical site. The vessels may be severed downstream of the ligated portion. In some instances, the vessel may be ligated at two spaced apart areas and the portion of the vessel between the ligation removed. A primary reason for ligating vessels is to maintain the surgical site free from an excess of blood and to reduce blood loss in the patient. Also in certain surgical procedures wherein tumors or parts of organs and the like are to be removed, the tumor or organ may have to be separated from certain vessels. Before separating the vessels are ligated. Once a blood vessel is completely shut off, hemostasis, that is, the natural closing of the ligated end of the vessel so as to stop blood flow, will occur in several days depending on the vessel. The body, in the meantime, will continue to allow blood flow around the ligated area through appropriate capillaries and secondary vessels with the natural physiological function of the body enlarging these by-pass vessels until adequate blood flow is obtained. Hence, when ligating the vessel, there should be positive stopping of the blood flow in the main vessel; that is, no leakage which might cause blood loss in the patient and may also disrupt the natural hemostasis and concurrent manufacture of new paths of blood flow in the patient.

In the past, this closing of the vessel was usually accomplished using ligatures; i.e., threads or filaments which the doctor tied around the vessel desired to be closed. This is a time consuming process and one wherein positive closure of the vessel is not always accomplished. In recent years, hemostatic clips have replaced ligatures in many surgical procedures to close blood vessels and other fluid ducts. Very often these hemostatic clips are narrow U or V shaped strips formed of tantalum or stainless steel which are capable of being deformed and possess sufficient strength to retain the deformation when clamped about a blood vessel.

In co-pending commonly assigned patent application, Ser. No. 276,131 filed June 22, 1981 and Ser. No. 282,461 filed July 31, 1981 there are disclosed hemostatic clips made from bio-compatible polymeric materials which are absorbable or non-absorbable in body tissue. These clips comprise a pair of leg members connected at their proximal ends by a resilient hinge section and terminating at their distal ends in a locking latch means. The distal end of one of the leg members comprises a deflectable hook section. The distal end of the other leg member is configured to be engaged by the hook section when the leg members are pivoted about the hinge to close the clip about a blood vessel. These clips as described have been found satisfactory for ligating most blood vessels. However, in certain instances if the vessel is large and the pressure in the vessel great, the clips may fail. The failure usually occurs at the latch or hook section. In certain instances, sufficient pressure is placed between the vessel clamping surfaces of the legs of the clip that the hook section will deflect allowing the opposite leg to spring out from underneath the hook member and the clip open.

SUMMARY OF THE PRESENT INVENTION

We have discovered a new and improved hemostatic clip made from bio-compatible polymeric materials which comprise a pair of leg members connected at their proximal ends by a resilient hinge section and having a deflectable hook type latching means.

The hemostatic clips of the present invention have good in vivo strength properties and have vessel clamping surfaces with minimal or no gap or in certain instances a controlled gap between the surfaces when the clip is in the closed position to provide positive clamping of vessels and, hence, obtain the desired hemostasis within the period of time of from about 3 to 5 days. The latching means becomes secure or more secure the greater the pressure placed on the vessel clamping surfaces which ensures that the clip remains in the closed and locked position in use.

The hemostatic clips of the present invention comprise first and second leg members joined at their proximal ends by resilient hinge means and terminating at their distal ends in latching means. The hinge section according to the present invention is resilient; i.e., it has elastic memory and acts as a spring which assists in the packaging of the clip as well as the handling and placement of the clip.

Each leg member has an outer surface and a vessel clamping inner face. The vessel clamping inner face is in opposition to a vessel clamping inner face of the other leg member. When the clip is in the closed position, there is a minimal or no gap or in certain instances a controlled gap between the vessel clamping faces. One leg member terminates at its distal end in a portion of the latch means. This portion comprises a deflectable hook member extending from the inner face of the leg member. The hook member has an inner face spaced from the inner face of the leg members and in certain embodiments substantially parallel thereto. In a preferred embodiment of the present invention, the end face of the hook member is beveled so as to form an acute angle with the inner face of the hook member. The other leg member terminates at its distal end in a complementary locking portion of the latch. This portion comprises an end face which fits underneath the hook member of the other leg. In a preferred embodiment, the end face of the other leg member has a bevel complementary to the bevel on the end face of the hook member. The complementary bevel forms an obtuse angle with the inner face of the second leg member and is adapted to deflect the hook member as the clip is closed.

The clip is closed by pivoting the leg members about the hinge means. The distal end of one leg member deflects and engages the hook member of the other leg member to lock the clip in the closed position. The leg members of our new clip are configured so when the clip is in the closed position the bending of the leg member carrying the hook member is greater than the bending of the opposite leg member. In use, this difference in bending causes the hook member to be urged towards the hinge means and secures the clip in the closed position. The greater the pressure placed on the vessel clamping surface of the leg member carrying the hook member, the more the hook member is urged towards the resilient hinge means and the tighter and more secure the clip becomes. In certain embodiments of the present invention, the vessel clamping surface of the leg member carrying the hook member has a concave radius of curvature extending from the hinge means to the hook member while the vessel clamping surface of the other leg member has a convex radius of curvature extending from the hinge means to the distal end of the member. The radius of the curvature of the vessel clamping surface of the latter leg member is smaller than the radius of curvature of the vessel clamping surface of the leg member carrying the hook member. In other embodiments of the present invention, the vessel clamping surface of the leg member carrying the hook member may be straight while the vessel clamping surface of the other leg member has a convex radius of curvature. In still other embodiments of the present invention, the vessel clamping surface of the leg member carrying the hook member is concave while the vessel clamping surface of the opposite leg member is straight. When using this latter embodiment a controlled gap is produced between the vessel clamping surfaces. This controlled gap embodiment is especially useful in the ligation of larger size blood vessels.

In yet other embodiments of the present invention, the area moment of inertia of the leg member carrying the hook member is less than the area moment of inertia of the other leg member. This may be accomplished by reducing the cross-sectional area of the leg member carrying the hook member and increasing the cross-sectional area of the other leg member. By decreasing or varying the area moments of inertia, one can control the amount of force placed on the vessel clamping surface and, hence, bend the leg member carrying the hook member to a greater degree than the other leg member in accordance with the present invention. A preferred embodiment of the clip of the present invention is to have the vessel clamping surfaces of both leg members with a convex radius of curvature. This double convex configuration provides a squeezing force to the vessel equivalent to a clip having a greater moment of inertia thus allowing for a reduction of the bulk of the clip and the amount of material placed in the body.

The outer surfaces of the leg members carry suitable means for allowing the clip to be picked up in the jaws of an appropriate forceps type hemostatic clip applier and closed about the vessel. In certain embodiments of the present invention this may be accomplished merely by providing the outer surface with an appropriate radius of curvature so that it will be held in the jaws of a forceps type clip applier. In preferred embodiments of the present invention, the outer surfaces include bosses extending transverse of the leg members which are adapted to fit into channels disposed in the jaws of a forceps type clip applier and are used to pick up the clip and close the clip about a blood vessel. In certain embodiments of the improved clip of the present invention, the legs of the clips include interlocking means which prevent relative transverse movement between the vessel clamping surfaces when the clip is in the closed position.

BRIEF DESCRIPTION OF THE DRAWINGS

The present invention will be described in greater detail in conjunction with the accompanying drawings wherein.

DESCRIPTION OF THE PREFERRED EMBODIMENTS

Figure 1:
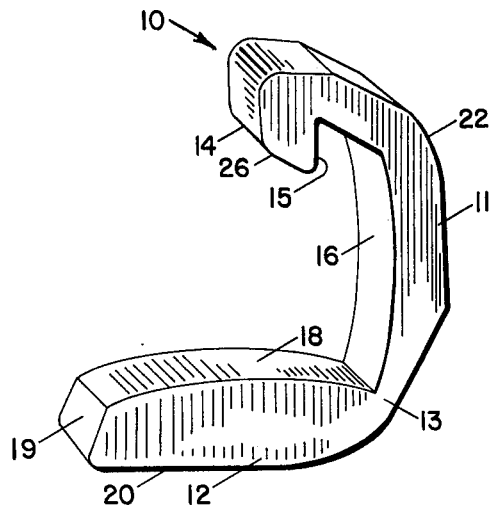
FIG. 1 is a greatly enlarged view in perspective of a hemostatic clip in accordance with the present invention.
Figure 2:
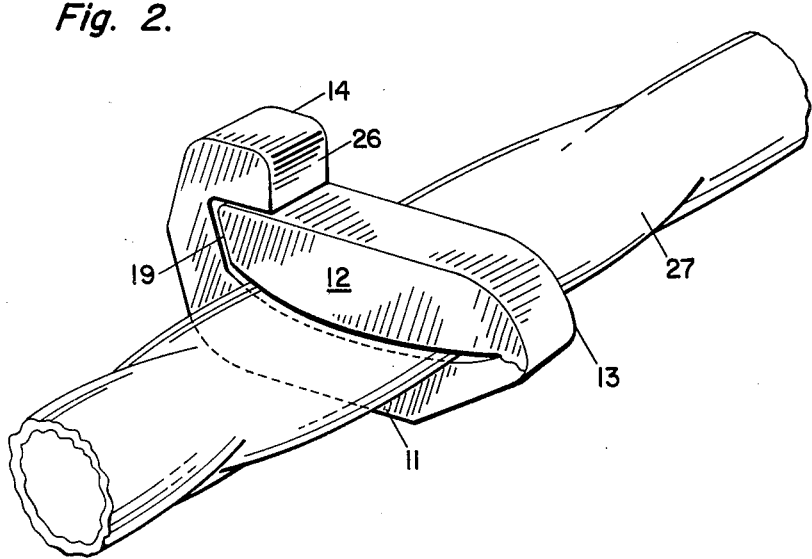
FIG. 2 illustrates the clip of FIG. 1 clamped about a blood vessel.

Referring to FIG. 1, there is shown a hemostatic clip 10 of the present invention. The hemostatic clip comprises two leg members 11 and 12. The leg members are connected at their proximal ends by the resilient hinge section 13. Leg member 11 terminates at its distal end in a hook member 14. The hook member has an inner face 15. In a preferred embodiment, the end surface of the hook member is beveled at 26 to assist in deflecting the hook member when the clip is closed. The vessel clamping surface 16 of the leg member 11 has a concave radius of curvature extending from the hinge to the start of the hook member. The other leg member 12 has vessel clamping surface 18 which has a convex radius of curvature extending from the hinge to the distal end of the leg member. The radius of curvature of the clamping surface 18 is smaller than the radius of curvature of clamping surface 16. Leg member 12 terminates in an end surface 19. Preferably this end surface is beveled and has a complementary bevel to the bevel on the hook member so as to assist in the deflection of the hook member when the clip is closed. The outer surfaces of the clip 20 and 22 are configured so as to be accepted by the jaws of a suitable forceps type applier and to allow those jaws to put pressure on the outer surfaces of the clip to close the clip. The clip is closed about a blood vessel as shown in FIG. 2 by urging the distal ends of the two leg members together until the end surface 19 of the leg member 12 deflects the hook member 14 by engaging end surface 26 of the hook member on leg 11 as the two leg members are pivoted about the resilient hinge 13 and closed about the blood vessel 27.

Figure 3:
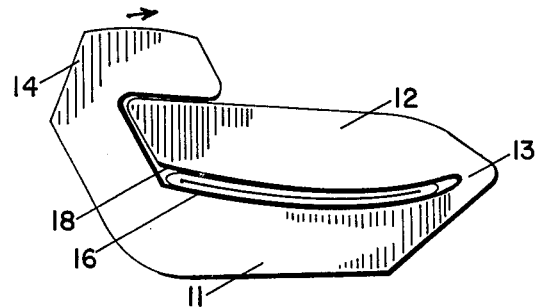
FIG. 3 is a cross-sectional view showing the clip of FIG. 1 closed about a blood vessel.

As is more clearly shown in FIG. 3, which is a cross-section of the closed clip, the radius of curvature of the vessel clamping convex surface 18 of the leg member 12 is smaller than the radius of curvature of the concave vessel clamping surface 16 of the leg member 11 carrying the hook member 14. The bulkier the closed blood vessel the more force is developed between the vessel clamping surfaces, and the more the clamping surface 16 of the leg member carrying the hook member is forced into a more concave position, thus drawing the hook member in the direction of the arrow towards the resilient hinge 13 and the more secure the clip becomes.

Figure 4:
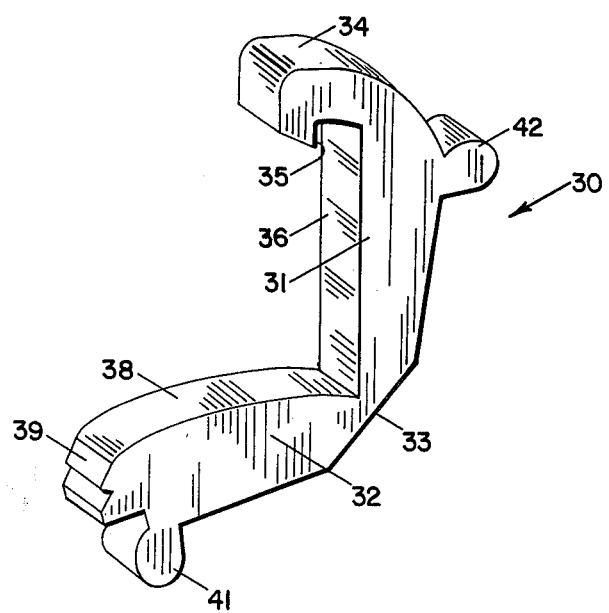
FIG. 4 is a greatly enlarged view in perspective of another embodiment of a hemostatic clip according to the present invention.

In FIG. 4 there is shown another embodiment of a hemostatic clip 30 of the present invention. The hemostatic clip is constructed of two leg members 31 and 32 connected at their proximal ends by hinge section 33. The leg 31 terminates at its distal end in a hook member 34. The hook member has an inner face 35 substantially parallel to the vessel clamping surface 36 of the leg. The vessel clamping surface 36 of the leg is substantially straight. The leg member 32 terminates at its distal end in an end face 39. The vessel clamping surface 38 has a convex radius of curvature. When legs 31 and 32 are pivoted about hinge 33 to bring vessel clamping surfaces 38 and 36 together, the hook 34 is deflected by the surface 39 of the leg 32 until the distal end of leg 32 snaps under hook 34 and is thereby locked in place. The convex radius of curvature of vessel clamping surface 38 places pressure on the surface 36 when the clip is in the closed position. This pressure urges the hook member towards the resilient hinge portion to insure that the clip remains closed during use and more securely retains the vessel.

Disposed on the outer surface of each leg member are cylindrical bosses 41 and 42. The bosses are used to manipulate the clip in a suitable instrument as will be described in conjunction with FIGS. 6 and 7.

Figure 5:
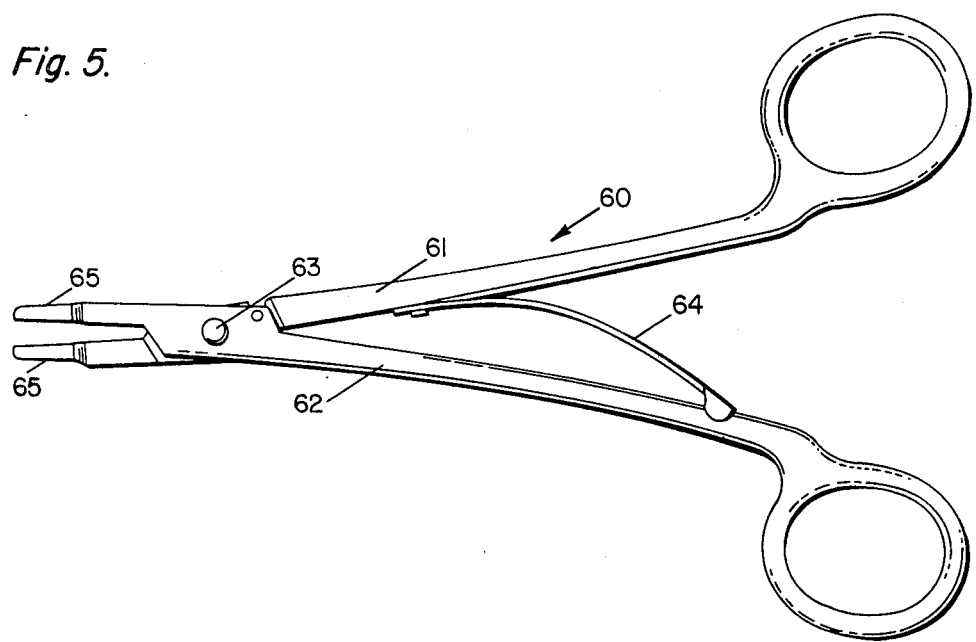
FIG. 5 illustrates a forceps type applier useful with the clips of the present invention.

FIG. 5 illustrates a forceps type ligating clip applier 60 comprising two handle members 61 and 62 crossing at a hinge point 63 and maintained in a normally open position by a spring 64. One handle extends beyond the hinge forming a jaw member 65 while the extension of the other handle also forms a corresponding jaw member 65.

Figure 6:
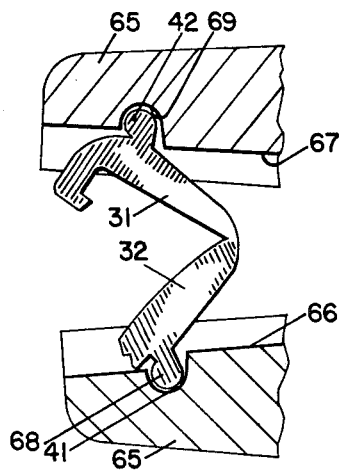
FIG. 6 illustrates the clip of FIG. 4 retained in the jaws of a forceps type clip applier.
Figure 7:
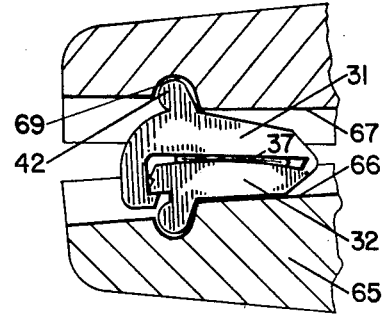
FIG. 7 illustrates the clip of FIG. 4 closed and locked over a blood vessel in the jaws of the applier.

FIG. 6 illustrates the detailed construction of the jaws and the interaction of the jaws with the clip of FIG. 4. The jaws are of identical design and are provided respectively with channels 66 and 67 extending rearwardly from the tips of the jaws. Each channel is provided with a cylindrical recess 68 and 69 disposed transverse of the channel and near the distal end thereof. The recesses are in alignment when the jaws of the applier are closed and are sized to receive the cylindrical lugs or bosses 41 and 42 of the clip. The channels forward of the recesses are deeper than to the rear of the recesses as illustrated in FIG. 6. When the open clip is held in the applier, the cylindrical bosses on the clip extend into the cylindrical recesses in each jaw. Due to the angle of the clip in the applier, the distal ends of the legs extend into the deeper or forward section of each jaw. The resilient or elastic memory of the hinge retains the clip in the recesses of the applier. The clip is initially loaded in the applier in a position as illustrated in FIG. 6. As shown in FIG. 7, the jaws 65 of the applier have been moved and the clip positioned over the vessel 37 to be ligated. The jaws of the applier are closed and the clip is locked over the vessel. As the clip is closed, the cylindrical lugs or bosses 41 and 42 of the legs rotate journal like in the cylindrical recesses 68 and 69 of the jaws. After the clip has been securely latched over the vessel to be ligated, the jaws of the applier are opened to release the clip and vessel and a new clip is loaded in the applier. Since the jaws of the applier and the clip pick up features are identical, it is not necessary to orient the applier to the clip when loading the applier.

Figure 8:
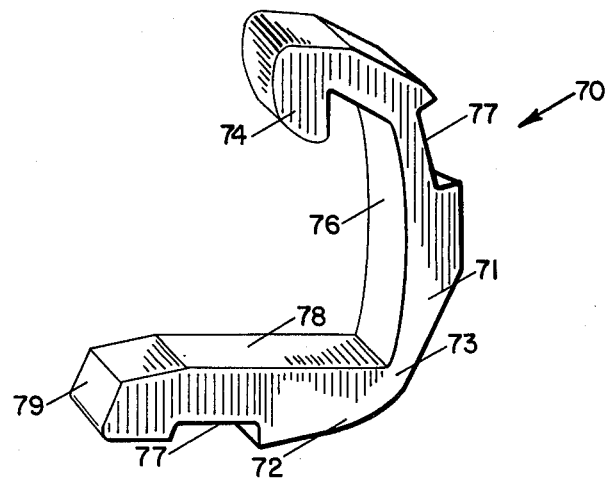
FIG. 8 is a greatly enlarged view in perspective of another embodiment of a hemostatic clip according to the present invention.

Referring to FIG. 8 there is shown another embodiment of a hemostatic clip of the present invention. In this embodiment, the clip 70 comprises a pair of leg members 71 and 72 connected at their proximal ends by a resilient hinge section 73. The leg member 71 terminates at its distal end in a return engaging hook member 74. The vessel clamping surface 76 of this leg member has a concave radius of curvature extending from the resilient hinge to the start of the deflectable hook member. The opposite leg member 72 has its distal end terminating in a beveled portion 79 adapted to deflect the hook member of the other leg. The vessel clamping surface 78 of this leg member is straight. This configuration produces a gap between the vessel clamping surfaces when the clip is closed. The gap is controlled by the degree of concavity in the leg member carrying the hook. This embodiment is for use with the larger and more massive blood vessels. In this embodiment, the outer surfaces of the leg members carry appropriate recesses 77 which will fit into corresponding bosses in the jaws of a clip applier.

Figure 9:
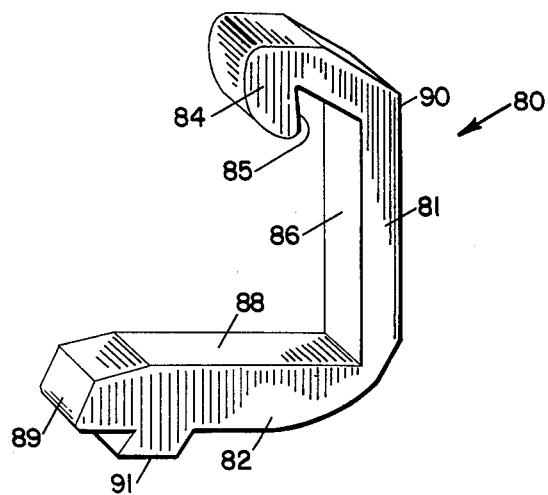
FIG. 9 is a greatly enlarged view in perspective of yet another embodiment of a hemostatic clip according to the present invention.
Figure 10:
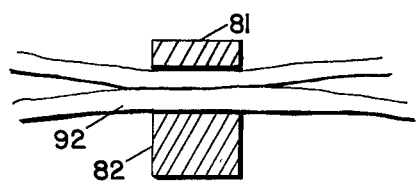
FIG. 10 is a cross-sectional view of the type of clip depicted in FIG. 9.

In FIG. 9 there is shown still another embodiment of a hemostatic clip of the present invention. In this embodiment, the clip 80 comprises a pair of leg members 81 and 82 connected at their proximal ends by a resilient hinge section 83. The leg member 81 terminates at its distal end in a return hook member 84. The inner surface 85 of the hook member is substantially parallel to the vessel clamping surface 86 of the leg. The vessel clamping surface of the leg member 81 is straight. The corresponding leg member 82 terminates at its distal end in a beveled surface 89 adapted to deflect the hook member 84 when closing the clip. The vessel clamping surface 88 of this leg member is also straight and will be substantially parallel to the vessel clamping surface 86 when the clip is in a closed position. The outer surface 90 of the leg member 81 is curved to be accepted by the jaws of a suitable forceps type closing instrument while the outer surface of the other leg member 82 carries a boss 91 to be accepted by the opposite jaw of the forceps type clip applier. As is shown in FIG. 10, which is a cross-sectional view of the clip shown in FIG. 9 closed and in place about a blood vessel 92, the cross-section of the leg member 81 carrying the hook member is substantially less than the cross-section of the other leg member 82.

This reduces the area moment of inertia of the leg member carrying the hook member. When the clip is clamped about a blood vessel, the pressure applied to the leg member 81 carrying the hook member tends to deflect that leg member to a greater degree than the opposite leg member 82 and continually urges the hook member towards the resilient hinge means, securing the clip in the closed position.

Figure 11:
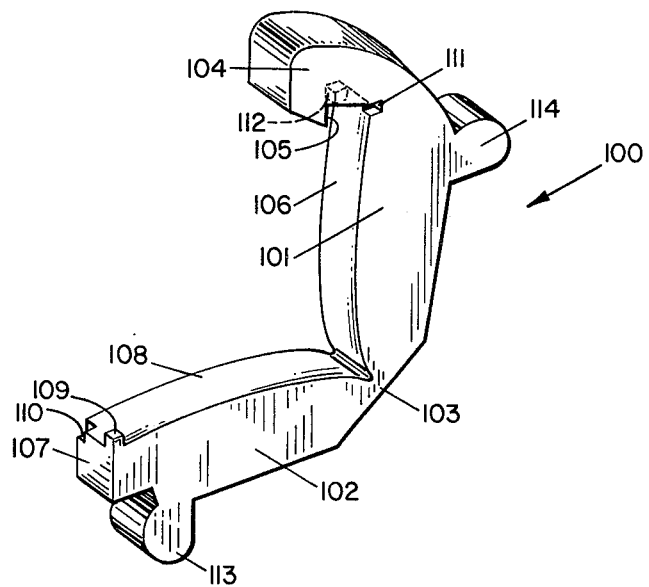
FIG. 11 is a greatly enlarged view in perspective of another embodiment of a clip according to the present invention.

In FIG. 11 there is shown a preferred embodiment of a hemostatic clip of the present invention. The clip 100 comprises a pair of leg members 101 and 102 connected at their proximal ends by hinge section 103. The leg 101 terminates at its distal end in a hook member 104. The hook member has an inner face 105 substantially parallel to the vessel clamping surface 106 of the leg. The vessel clamping surface 106 has a slightly convex curved surface. The leg member 102 terminates at its distal end in end face 107. The vessel clamping surface 108 also has a slightly convex radius of curvature. At the end of the vessel clamping surface 108 there is an ear 109 and a recess 110. Upon closing of the clip (as previously described in conjunction with FIG. 4) the ear 109 and recess 110 cooperate with a complimentary recess 111 and ear 112 disposed in vessel clamping surface 106. The engagement of the complimentary ears and recesses prevent lateral movement between the leg members when the clip is in the closed position. Disposed on the outer surface of each leg member are cylindrical bosses 113 and 114 which are used to manipulate and place the clip.

The clips of the present invention may be constructed in various sizes according to their intended function. Hemostatic clips are usually less than 6 millimeters in length, about 1½ millimeters in width and have a vessel clamping surface of about 3 millimeters in length. The dimensions of the clip may be reduced by about 50% for certain applications in microsurgery. Larger clips for special hemostatic applications and other functions such as closure of ova ducts or vasdeferens may have dimensions of about double those of a typical hemostatic clip. The various sizes of the clip are preferably matched with individual appliers having jaws tailored to the size of the clip for best performance.

The clips of the present invention are most conveniently molded of biologically acceptable polymeric materials which may be absorbable or non-absorbable by body tissue. Preferred absorbable polymers include homopolymers and copolymers of glycolide and lactide and poly(p-dioxanone). Preferred non-absorbable polymers include nylon, polyester, and polypropylene. All these materials have been demonstrated to be biologically acceptable when used as sutures or other implantable medical devices.

The clips of the present invention are preferably formed in an open position and may be easily and economically manufactured by injection molding or other suitable techniques.

Having now described the present invention and certain specific embodiments thereof, it will be readily apparent to one skilled in the art that many variations and modifications may be made to the present invention without departing from the spirit and scope thereof.

What is claimed is:

1. A hemostatic clip comprising first and second leg members joined at their proximal ends by resilient hinge means and terminating at their distal ends in latch means, each leg member having an outer surface and a vessel clamping inner surface, said vessel clamping inner surace being in opposition to the vessel clamping inner surface of the other leg member, the outer surface of each leg member being configured to be accepted by the jaws of a clip applier wherby the clip may be clamped about a vessel, said first leg member terminating at the distal end thereof in a portion of the latch means, said portion comprising a deflectable hook member extending from the inner face of said leg member, said hook member having an inner surface spaced from the inner surface of said leg member, said second leg member terminating at the distal end thereof in a complementary locking portion of the latch means whereby when said first and second leg members are pivoted about said hinge means, the distal end of said leg member deflects and engages the hook member of the first leg member to lock the clip in a closed position, the vessel clamping surface of said first leg member having a concave radius of curvature between the hinge means and the hook member and the vessel clamping surface of the second leg member having a convex radius of curvature between the hinge means and its distal end, the radius of curvature of the vessel clamping surface of said second leg member being smaller than the radius of curvature of the vessel clamping surface of said first leg member whereby hook member is urged towards the hinge means when pressure is placed on the vessel clamping surfaces of the leg members when the clip is in the closed position to aid in securing the clip in the closed position.

2. The clip according to claim 1 wherein the radius of curvature on said vessel clamping surfaces extend uniformly from the hinge means to the distal ends of the leg members.

3. The clip according to claim 1 wherein the outer surfaces of the leg members include cylindrical bosses extending transverse of the outer surface and being positioned to be engaged by the jaws of a suitable forceps type clip applier.

4. The clip according to claim 1 or 3 including means for preventing lateral movement between the leg members when the clip is in the closed position.

* * * * *